United States Patent
Fang et al.

(10) Patent No.: US 9,131,948 B2
(45) Date of Patent: Sep. 15, 2015

(54) ASSISTANT DEVICE AND GUIDING ASSEMBLY FOR PERCUTANEOUS SURGERY

(71) Applicant: NATIONAL CHENG KUNG UNIVERSITY, Tainan (TW)

(72) Inventors: Jing-Jing Fang, Tainan (TW); Ruey-Mo Lin, Tainan (TW); Hao-Chuan So, Taichung (TW); Sheng-Min Lan, Tainan (TW); Tzu-Chieh Wu, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 32 days.

(21) Appl. No.: 13/971,420

(22) Filed: Aug. 20, 2013

(65) Prior Publication Data
US 2014/0066940 A1 Mar. 6, 2014

(30) Foreign Application Priority Data

Aug. 31, 2012 (TW) .............................. 101131851 A

(51) Int. Cl.
| | |
|---|---|
| A61B 17/58 | (2006.01) |
| A61B 17/60 | (2006.01) |
| A61F 2/00 | (2006.01) |
| A61B 17/17 | (2006.01) |
| A61B 17/16 | (2006.01) |
| A61B 17/34 | (2006.01) |
| A61B 19/00 | (2006.01) |
| A61B 17/84 | (2006.01) |

(52) U.S. Cl.
CPC .......... *A61B 17/1757* (2013.01); *A61B 17/1671* (2013.01); *A61B 17/3403* (2013.01); *A61B 19/201* (2013.01); *A61B 17/848* (2013.01); *A61B 2017/3407* (2013.01); *A61B 2019/461* (2013.01); *A61B 2019/467* (2013.01)

(58) Field of Classification Search
USPC ...................................... 606/96–98
See application file for complete search history.

(56) References Cited

U.S. PATENT DOCUMENTS

| | | |
|---|---|---|
| 6,530,930 B1 | 3/2003 | Marino et al. |
| 8,623,022 B2 * | 1/2014 | Forton et al. ................ 606/86 R |
| 2002/0007188 A1 | 1/2002 | Arambula et al. |
| 2005/0216026 A1 | 9/2005 | Culbert |
| 2005/0267481 A1 | 12/2005 | Carl et al. |
| 2006/0084844 A1 | 4/2006 | Nehls |

\* cited by examiner

*Primary Examiner* — Sameh Boles
(74) *Attorney, Agent, or Firm* — Muncy, Geissler, Olds & Lowe, P.C.

(57) ABSTRACT

An assistant device for percutaneous puncture is disclosed. The assistance device includes a fixing element, a first rotatable element, a supporting element and a second rotatable element. The fixing element has a first rail, and the first rotatable element is slidably disposed on the first rail. The supporting element is connected to the first rotatable element. The second rotatable element is slidably disposed on the supporting element and has a puncture restraint pore.

8 Claims, 10 Drawing Sheets

ASSISTANT DEVICE AND GUIDING ASSEMBLY FOR PERCUTANEOUS SURGERY

CROSS REFERENCE TO RELATED APPLICATIONS

This Non-provisional application claims priority under 35 U.S.C. §119(a) on Patent Application No(s). 101131851 filed in Taiwan, Republic of China on Aug. 31, 2012, the entire contents of which are hereby incorporated by reference.

BACKGROUND OF THE INVENTION

1. Field of Invention

The present invention relates to an assistant device for percutaneous puncture and a guiding assembly for percutaneous surgery.

2. Related Art

The spine is the support of human skeleton, and more important, it can protect the inside spinal cord. The spinal cord is the center of human nerves, and the nerves extend outward from the inside of the spine and are spread to the organs of human body as well as the tails of the distal limbs. Therefore, the spine could be called a starting point of the human body's neural network. The common spinal lesions include injuries caused by external forces, degenerative diseases (such as spinal disc herniation, spondylolisthesis, etc.), lumbar scoliosis, and osteoporosis. Currently, the treatment for mild-to-moderate spinal lesions usually includes drugs and physical therapy, but for the moderate-to-heavy spinal lesions, the surgical treatment is selected.

The treatment of spinal surgery can be simply divided into "clearing" the bony spur, intervertebral discs and fragments of broken bone, which compress the nerves, and "implanting" the bony fusion material, bone cement, fixator or artificial joint. However, due to the spinal nerve roots connect to the brain and body, the nervous system is destroyed, which may cause huge damages to the body, as long as a small mistake in the spinal surgery. Therefore, the safety of the surgery has been the most valued issue.

Since the shapes of the spinal segments are mutually different and individual differences exist, it is an important factor in surgical safety to exactly put the implant into the spinal segment (or vertebral body). For this reason, various kinds of assistant devices have been used to improve safety of the spinal surgery. The assistant devices can be divided into percutaneous and non-percutaneous types. Generally, the percutaneous assistant devices include a K-pin (Kirschner pin) and an outer sleeve tube and are suitable for minimally invasive surgery and vertebroplasty. The doctor executes the surgical planning based on the X-ray images at first, and then directly punctures the K-pin into a predetermined spinal segment from the outer skin. Afterwards, a bone screw is implanted or the bony cement is injected via the outer sleeve tube.

However, the clinical practices, most K-pins and outer sleeve tubes must be held by hand. In other words, the doctor needs to perform the operations including puncturing, replacing surgical instruments and slightly adjusting the surgical planning, and at the same time, steady the position and angle of the assistant device during the surgery. Otherwise, any slight deviation would affect the surgery, even cause an irreversible damage. This situation not only makes the doctor tired, but imperceptibly extends the operation time and decreases accuracy of the operation.

For now, to confirm the puncture angle and position in surgery is still based on the experiences by the method of trial and error. In brief, it needs to successive adjust the puncturing positions in view of the X-ray or C-arm images for many times in the puncturing process, until the K-pin punctures through the vertebral pedicle and correctly into the vertebral body. Based on past experiences, a puncturing process needs at least ten times adjustments. That is, the operator needs to hold the K-pin and receives the radiation exposure for over ten times, so the impact for surgeon and patients is quite substantial. In addition, due to the assistant device needs to be held by hand and there is no accurate measurement reference for each adjustment, the operators must adjust the K-pin based on the personal experience and intuition. The beginners usually need longer operation time, and may still have insufficient accuracy.

Therefore, it is an important subject of the present invention to provide an assistant device for percutaneous puncture, which can be cooperated with other existing assistant devices such as k-pin and outer sleeve tube, and applied in percutaneous puncture surgery, so that the medical staffs do not need to constantly hold the K-pin. Preferably, it can also provide the functions of measurement and assisting the adjustment of the K-pin, thereby improving the stability and accuracy of the operation and thus shortening the operation time and increasing the operation safety.

SUMMARY OF THE INVENTION

In view of the foregoing subject, an objective of the present invention is to provide an assistant device for percutaneous puncture, which can be cooperated with other existing assistant devices such as k-pin and outer sleeve tube, and applied in percutaneous puncture surgery, so that the medical staffs do not need to constantly hold the K-pin. Preferably, it can also provide the functions of measurement and assisting the adjustment of the K-pin, thereby improving the stability and accuracy of the operation and thus shortening the operation time and increasing the operation safety.

Another objective of the present invention is to provide a guiding assembly for percutaneous surgery including a pin and a reaming member as well as the above-mentioned assistant device for percutaneous puncture, for stably and precisely positioning in height during the surgery, thereby enhancing the related spinal operation.

To achieve the above objective, the present invention discloses an assistant device for percutaneous puncture, which includes a fixing element, a first rotatable element, a supporting element, and at least a second rotatable element. The fixing element has a first rail, and the first rotatable element is slidably disposed on the first rail. The supporting element is connected to the first rotatable element. The second rotatable element is slidably disposed on the supporting element and has a puncture restraint pore.

To achieve the above objective, the present invention further discloses a guiding assembly for percutaneous surgery, which includes an assistant device for percutaneous puncture, pin and a reaming member. The assistant device for percutaneous puncture includes a fixing element, a first rotatable element, a supporting element, and at least a second rotatable element. The fixing element has a first rail, and the first rotatable element is slidably disposed on the first rail. The supporting element is connected to the first rotatable element. The second rotatable element is slidably disposed on the supporting element and has a puncture restraint pore. The pin is disposed through the puncture restraint pore, and the reaming member is mounted on the pin. To be noted, the reaming member of this invention is also called an outer thimble, which includes any member having the same or similar function as the reaming member or the outer thimble.

In one embodiment, the guiding assembly further includes an assistant restraint element having a pin restraint pore, and the assistant restraint element is disposed through the puncture restraint pore.

In one embodiment, the assistant device is cooperated with a pin, and the pin is disposed through the pin restraint pore.

In one embodiment, the assistant restraint element has a handheld portion.

In one embodiment, the supporting element has a distance mark portion.

In one embodiment, the first or second rotatable element has an angle mark portion.

In one embodiment, the assistant device comprises two second rotatable elements disposed at different sides of the fixing element.

In one embodiment, the fixing element or the second rotatable element has at least a fitting portion.

In one embodiment, the fixing element further has a plurality of receiving holes for receiving a plurality of pins.

In one embodiment, the first rotatable element is rotatable about a first axis, and the second rotatable element is rotatable about a second axis.

In one embodiment, the reaming member comprises a handheld portion and a drill portion.

As mentioned above, the assistant device for percutaneous puncture can be fixed on the back of a patient and cooperated with the pin and reaming member. By using the assistant device, the medical personnel does not need to hold the pin or reaming member all the time during the operation, thereby enhancing the stability and precision of the spinal surgery. More specific, the assistant device is helpful in guiding the pin to pedicles.

In the assistant device for percutaneous puncture, the first rotatable element is slidably disposed on the fixing element and the second rotatable element is slidably disposed on the supporting element, so that the first rotatable element is movable along a first axis and the second rotatable element is movable along a second axis. In practice, the operator can roughly place the assistant device around the target, and then fine adjust it for the precise operation. Moreover, the first rotatable element is rotatable about a first axis and the second rotatable element is rotatable about a second axis, so that the assistant device can adjust not only the puncture position but also the puncture angle, thereby precisely guiding the pin through the pedicle to reach the inside of vertebral body.

In addition, the supporting element is preferably configured with a distance mark portion, and the first or second rotatable element is preferably configured with an angle mark portion. Accordingly, the medical personnel can adjust or correct the puncture position and angle based on the numerical reference instead of doing these precise operations by the personal experience or intuition.

Moreover, the present invention is also helpful in reducing the radiation dose. In details, the assistant device for percutaneous puncture can provide a firmly and stably support, so that the medical personnel does not need to hold the pin all the time. Thus, the medical personnel can stay away from the operating table while taking X-ray or C-arm, thereby reducing the radiation dose took by the medical personnel. Regarding to the patient, since the adjusting and correcting times of the pin and the puncture can be decreased, the total operation times of taking X-ray or C-arm are also decreased so as to reduce the radiation dose took by the patient. As a result, this invention can efficiently reduce the radiation dose took by the medical personnel and patient.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
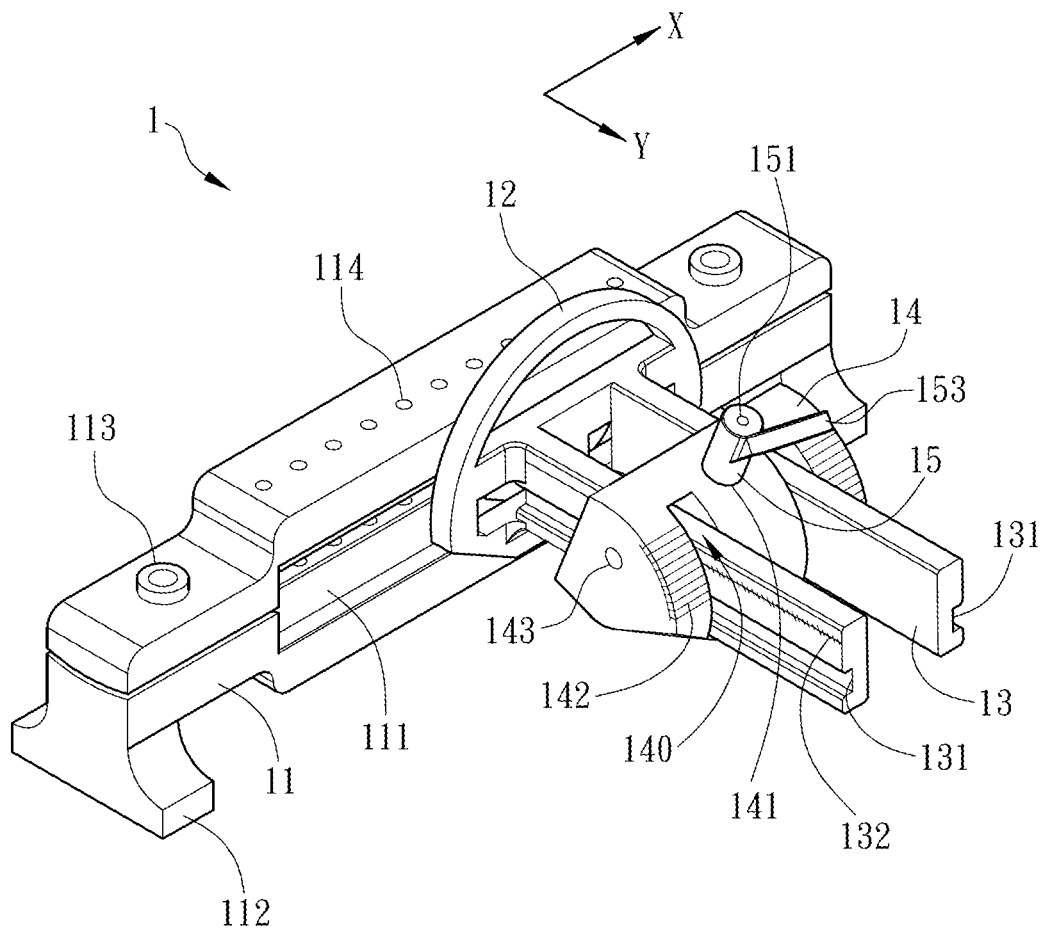
FIG. 1 is a schematic diagram showing an assistant device for percutaneous puncture according to a first embodiment of the invention.
Figure 2:
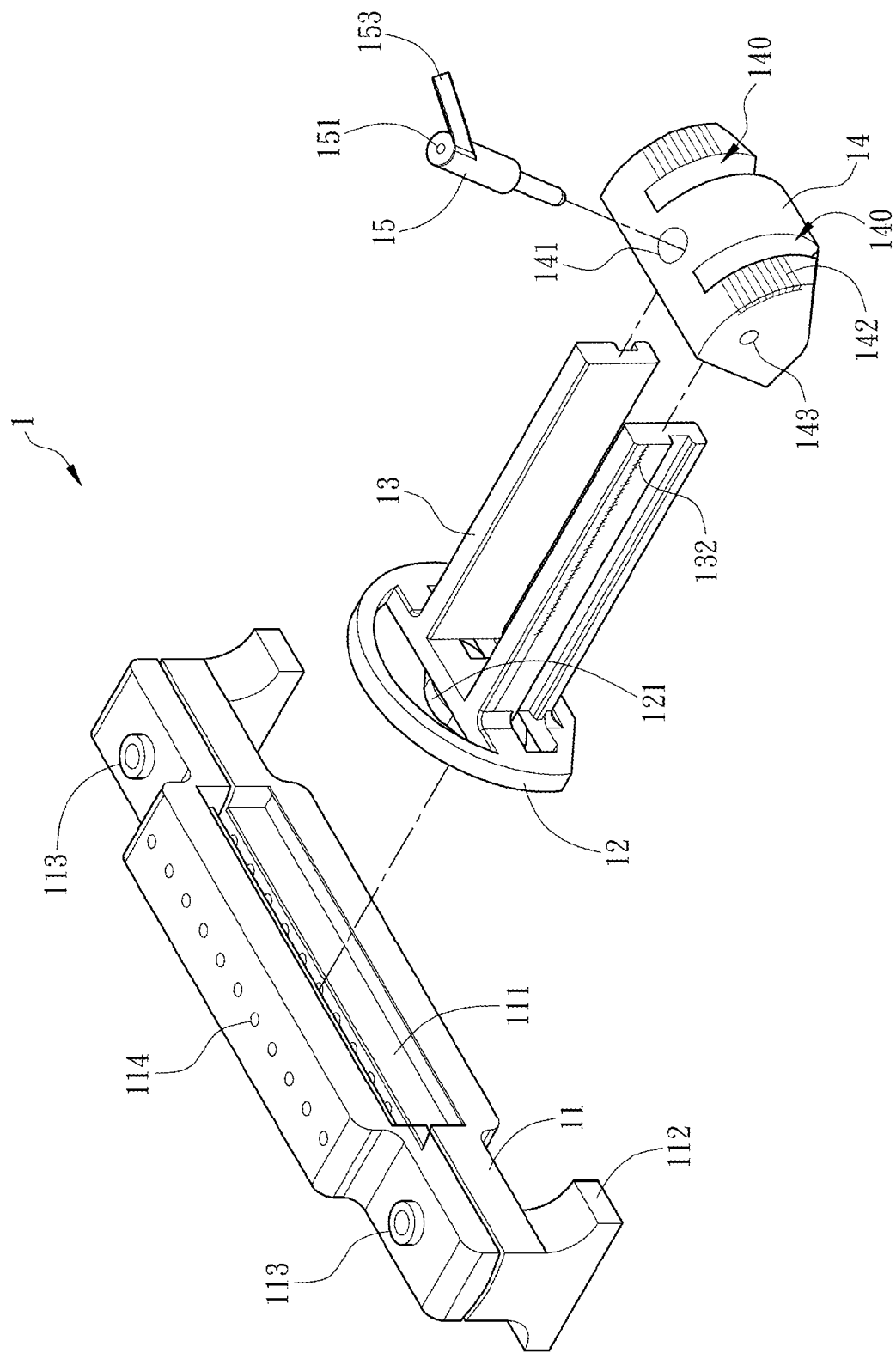
FIG. 2 is an exploded view of the assistant device for percutaneous puncture of FIG. 1.
Figure 8:
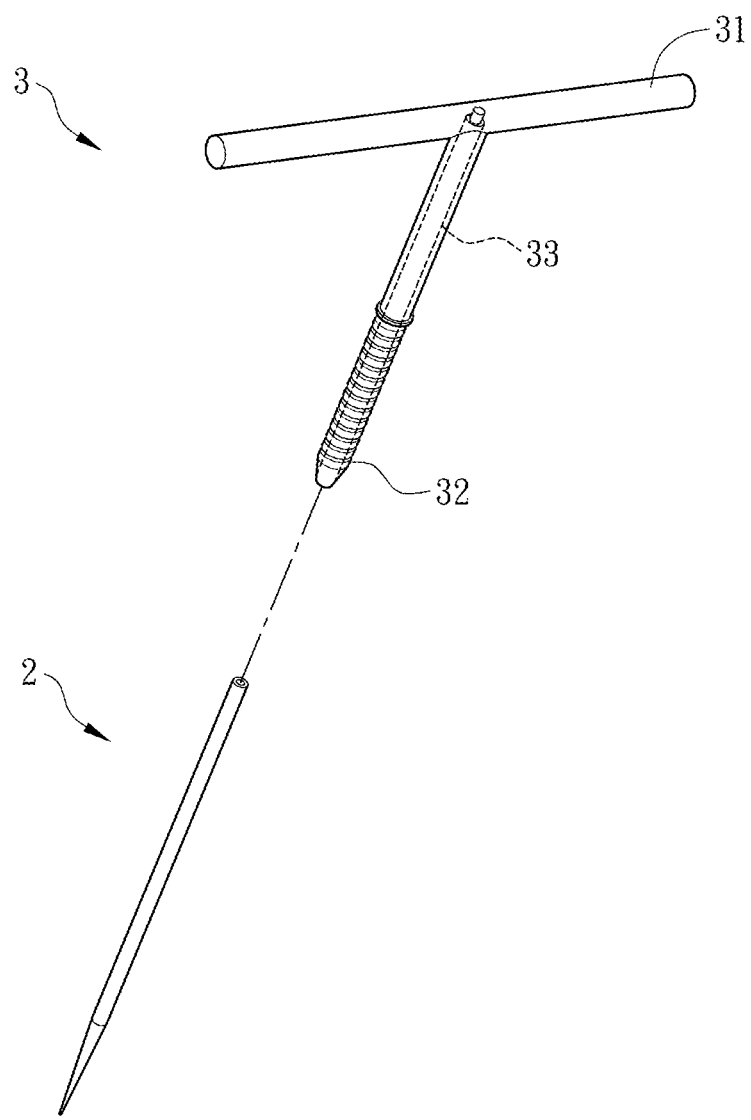
FIG. 8 is a schematic diagram showing a reaming member mounted on a pin.

FIG. 1 is a schematic diagram showing an assistant device for percutaneous puncture according to a first embodiment of the invention, FIG. 2 is an exploded view of the assistant device for percutaneous puncture of FIG. 1, and FIG. 8 is a schematic diagram showing a reaming member mounting on a pin. Referring to FIGS. 1, 2 and 8, the present invention discloses a guiding assembly G for percutaneous surgery, which includes an assistant device 1 for percutaneous puncture, a pin 2 and a reaming member 3. The reaming member 3 is also called an outer thimble, which includes any member having the same or similar function as the reaming member or the outer thimble. The assistant device 1 includes a fixing element 11, a first rotatable element 12, a supporting element 13, and at least a second rotatable element 14. The following illustrations will describe the structures and features of all elements of the assistant device 1, and then discuss the cooperation between the assistant device 1, the pin 2 and the reaming member 3.

Referring to FIGS. 1 and 2, the fixing element 11 has a first rail 111. The first rotatable element 12 is slidably disposed on the first rail 111, and the supporting element 13 is connected to the first rotatable element 12. In this embodiment, the supporting element 13 and the first rotatable element 12 are integrally formed as one piece so as to simplify the manufacturing procedure thereof and enhance the rigidity thereof. Of course, in other embodiments, the supporting element 13 and the first rotatable element 12 can be separated parts to be assembled later.

In this embodiment, the assistant device 1 includes only one second rotatable element 14, which is slidably disposed on the supporting element 13. For example, the supporting element 13 includes two long-shaped plates disposed parallel to the first rotatable element 12. The extending direction of the long-shaped plates is perpendicular to the extending direction of the first rotatable element 12. The second rotatable element 14 has two recesses 140, which allow the second rotatable element 14 to be disposed across the supporting element 13. Accordingly, the second rotatable element 14 can be moved on the supporting element 13 along the extending direction of the supporting element 13.

The second rotatable element 14 has a puncture restraint pore 141, which is configured for the pin 2 or its cooperated element (e.g. the following assistant restraint element 15) to penetrate through. The puncture restraint pore 141 is a long through hole connecting two sides of the second rotatable element 14.

The function of slidably disposing can be carried out by means of rails, grooves, wheels, beads, or gears. When the first rotatable element 12 moves on the first rail 111, the supporting element 13 can carry the second rotatable element 14 to move linearly along the second axis X. Besides, the supporting element 13 further includes a second rail 131, and the second rotatable element 14 is slidably disposed on the supporting element 13. In other words, the second rotatable element 14 can be moved on the second rail 131 linearly along the first axis Y.

The supporting element 13 has a distance mark portion 132 configured on the surface of the supporting element 13, which is contact with the second rotatable element 14. Since the distance mark portion 132 is parallel to the second rail 131, it can be used to measure the traveling distance of the moved second rotatable element 14 on the supporting element 13 along the first axis Y. Of course, the distance mark portion 132 can be embodied by any approaches and be disposed at any location that is easily observed. Similarly, it is possible to configure another distance mark portion 132 on the surface of the fixing element 11, which is contact with the first rotatable element 12. By measuring the traveling distance of the first rotatable element 12 along the second axis X, the linear movement of the second rail 132 on the second axis X can be indirectly obtained.

Accordingly, the assistant device 1 is capable of moving along the first axis Y and/or the second axis X. After the assistant device 1 is fixed on the back of the patient around the target position through the fixing element 11, the second rotatable element 14 is moved along these two axes X and Y so as to align the puncture restraint pore 141 as well as the pin 2, which is disposed through the puncture restraint pore 141, at the target position. More important, the doctor can easily adjust and correct the position of the puncture restraint pore 141 according to the surgery plan or operation requirement. Moreover, the doctor can take the distance mark portion 132 as a reference standard for the adjusting and correcting. The configuration of the distance mark portion 132 can provide a perfect reference in the adjusting and correcting operations, so that the operator does not need to perform the adjustment and correction based on the personal experience or intuition.

Figure 3A:
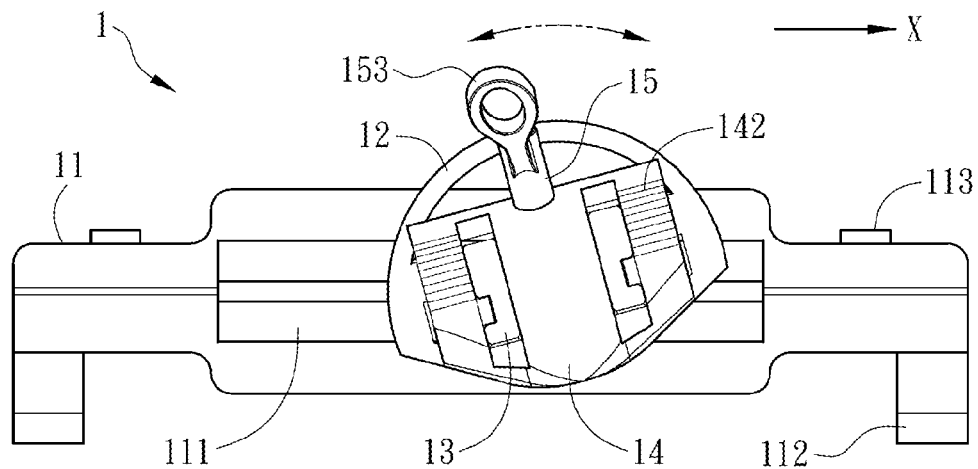
FIG. 3A is a schematic diagram showing the first rotatable element of FIG. 1 rotating about a first axis.
Figure 3B:
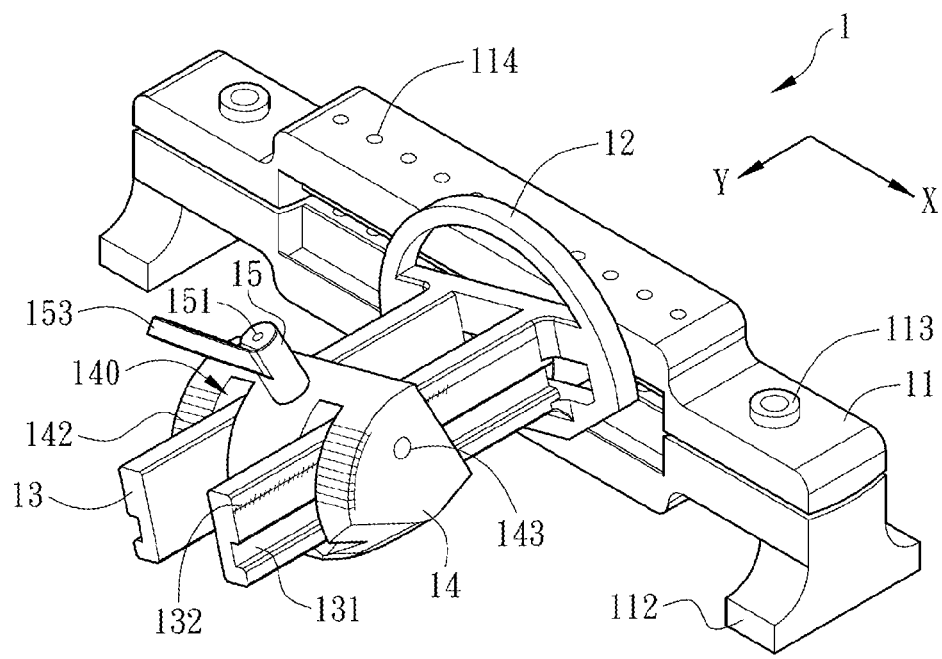
FIG. 3B is another perspective view of the assistant device for percutaneous puncture of FIG. 3A.

The first rotatable element 12 is capable of rotating about a first axis Y, and the second rotatable element 14 is capable of rotating about a second axis X, which is perpendicular to the first axis Y. FIG. 3A is a schematic diagram showing the first rotatable element of FIG. 1 rotating about a first axis, and FIG. 3B is another perspective view of the assistant device for percutaneous puncture of FIG. 3A. Referring to FIGS. 2, 3A and 3B, the first rotatable element 12 has an engaged portion 121, which is slidably disposed within the first rail 111 of the fixing element 11. Thus, the first rotatable element 12 is capable of rotating about the first axis Y and moving back and forth along the second axis X. Since the first rotatable element 12 and the supporting element 13 are connected, the rotating second rotatable element 14 can drive the supporting element 13 to rotate simultaneously.

Figure 4A:
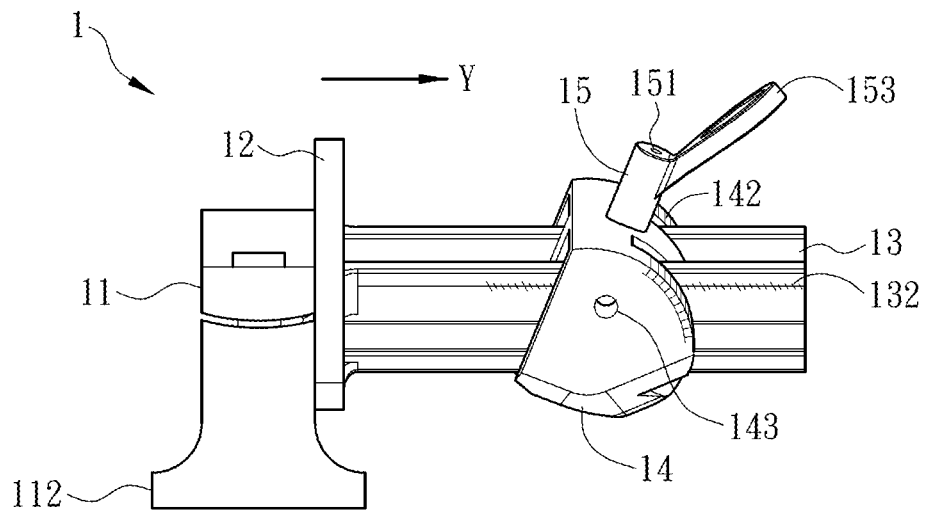
FIG. 4A is a schematic diagram showing the second rotatable element of FIG. 1 rotating about a second axis.
Figure 4B:
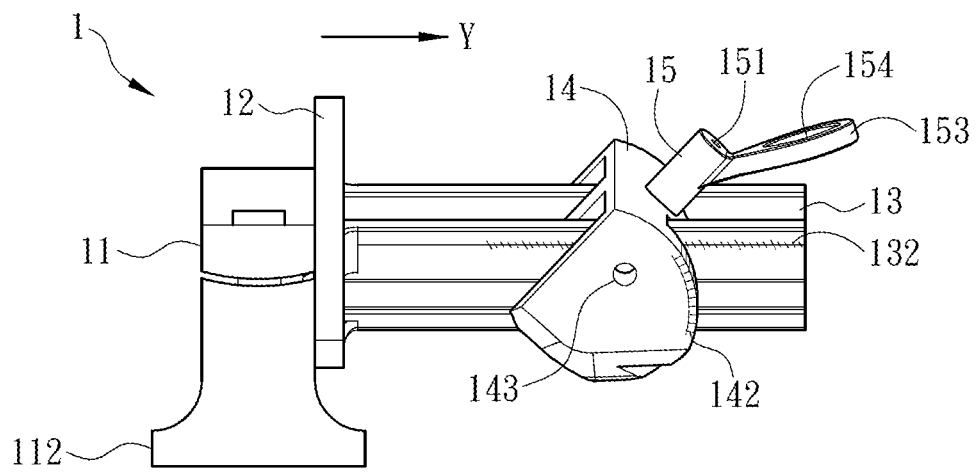
FIG. 4B is another perspective view of the assistant device for percutaneous puncture of FIG. 4A.

FIG. 4A is a schematic diagram showing the second rotatable element of FIG. 1 rotating about a second axis, and FIG. 4B is another perspective view of the assistant device for percutaneous puncture of FIG. 4A. With reference to FIGS. 2, 4A and 4B, the second rotatable element 14 is slidably disposed on the second rail 131 of the supporting element 13 through the recesses 140, and the second rotatable element 14 is capable of rotating about the supporting element 13. Herein, the second rail 131 extends along the first axis Y, so that the second rotatable element 14 is capable of rotating about the second axis X and moving back and forth along the first axis Y.

In this embodiment, each of the first rotatable element 12 and the second rotatable element 14 is configured with an angle mark portion 142 for providing more scale references. However, the configuration of the angle mark portion 142 is not limited. For example, only one angle mark portion 142 is configured on either the first rotatable element 12 or the second rotatable element 14; otherwise, no angle mark portion 142 is configured. The angle mark portion 142 of the second rotatable element 14 is disposed at the junction between the second rotatable element 14 and the supporting element 13. Accordingly, the distance mark portion 132 can also function as a pointer for simply indicating the rotation status of the second rotatable element 14. Preferably, the angle mark portion 142 is disposed with respective to the distance mark portion 132, so that the operator can check the references at the same time. Of course, in some embodiments, the first rotatable element 12 is configured with an angle mark portion 142, and the fixing element 11 is used as the basic reference for the scale of the angle mark portion 142. The configuration of the angle mark portion 142 can provide a reliable reference, so that the operator does not need to decide the puncture angle based on the personal experience or intuition. The reliable numerical reference provided by the angle mark portion 142 is helpful in reducing the adjusting and correcting times, thereby decreasing the possible received radiation dose.

Figure 5:
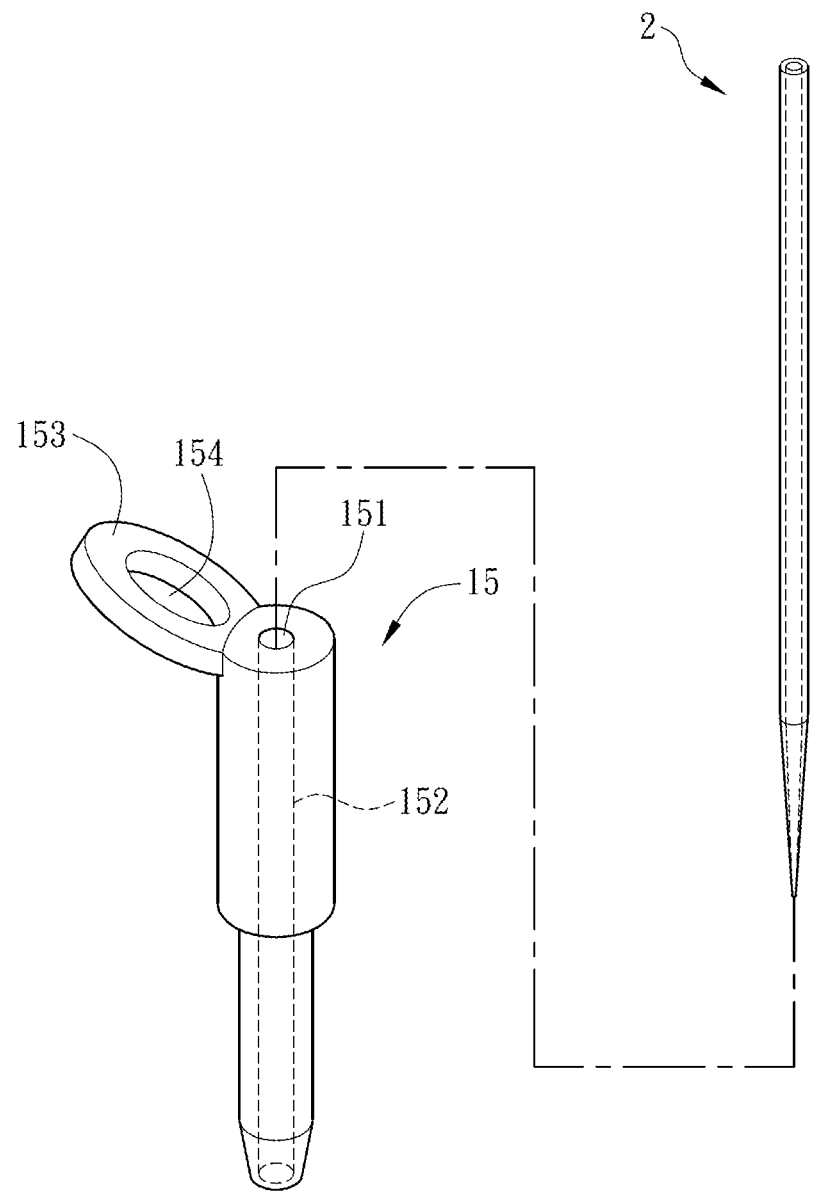
FIG. 5 is a schematic diagram showing a pin applied to the assistant restraint element of FIG. 2.

FIG. 5 is a schematic diagram showing a pin applied to the assistant restraint element of FIG. 2. The pin 2 and the reaming member 3 are used cooperated with the assistant device 1. Referring to FIGS. 1 to 2B, the assistant device 1 further includes an assistant restraint element 15, which has a pin restraint pore 151. The assistant restraint element 15 has a roughly column shape, and the bottom half thereof has proper inner diameter and shape for cooperating with the puncture restraint pore 141. The assistant restraint element 15 is disposed through the puncture restraint pore 141, and thus received within the second rotatable element 14. In addition, the top half of the assistant restraint element 15 has a slightly larger inner diameter for restricting the ratio of the assistant restraint element 15 to be inserted into the puncture restraint pore 141. Moreover, the assistant restraint element 15 further has a pin restraint channel 152 corresponding to the pin restraint pore 151. The pin restraint channel 152 penetrates through two ends of the assistant restraint element 15. The inner diameter and shape of the pin restraint channel 152 correspond to the pin 2 so that, in operation, the pin 2 is inserted into the pin restraint pore 151 and thus mounted and fixed in the pin restraint channel 152. Accordingly, the operator or doctor does not need to hold the pin 2 all the time. More important, the elements of the assistant device 1 allow the operator or doctor to easily and simply adjust the puncture position and angle.

In addition, the assistant restraint element 15 further includes a handheld portion 153. In practice, the operator or doctor can grab the handheld portion 153 so as to hold the assistant restraint element 15 steadily. This configuration can help to prevent the easy drop issue of the assistant restraint element 15 as it is wet by body fluid during the operation.

Figure 6A:
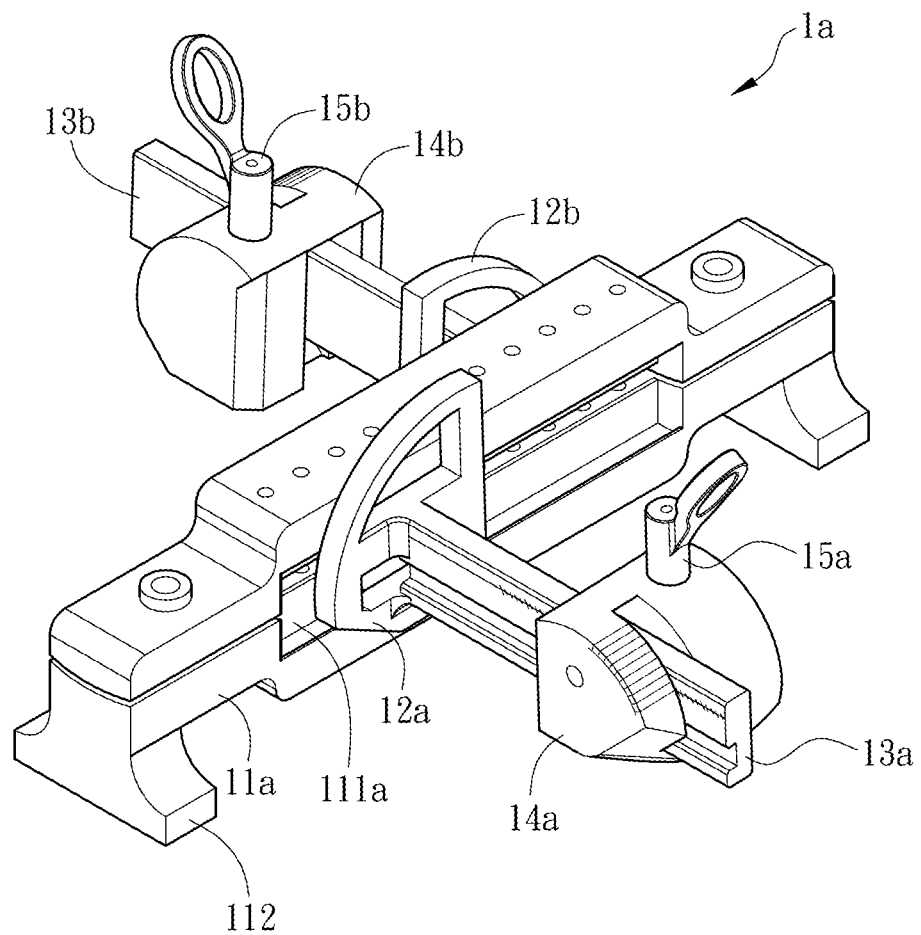
FIG. 6A is a schematic diagram showing an assistant device for percutaneous puncture according to a second embodiment of the invention.
Figure 6B:
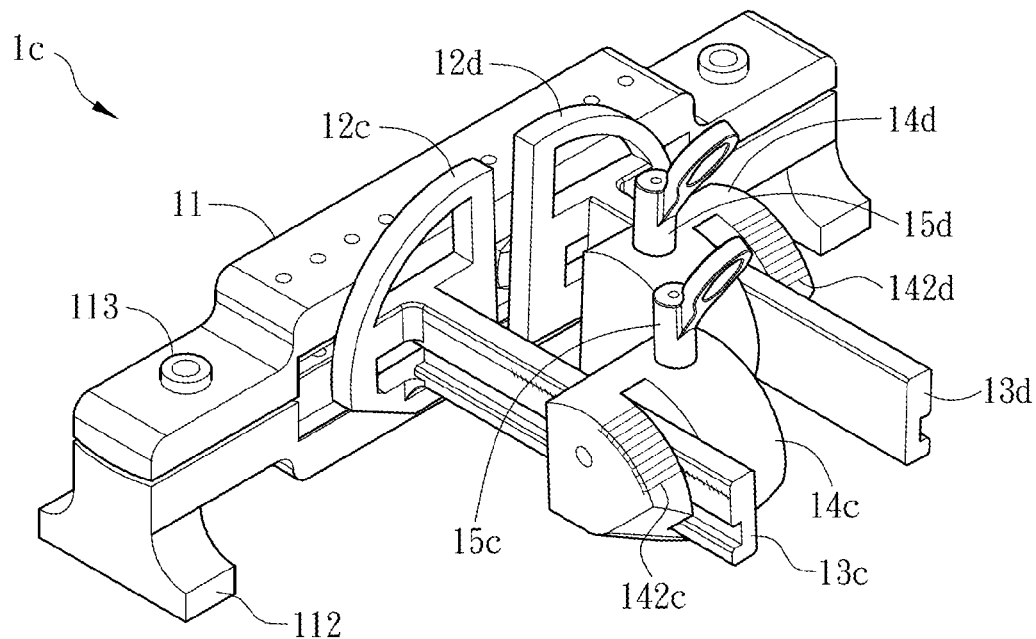
FIG. 6B is a schematic diagram showing an assistant device for percutaneous puncture according to a third embodiment of the invention.
Figure 6C:
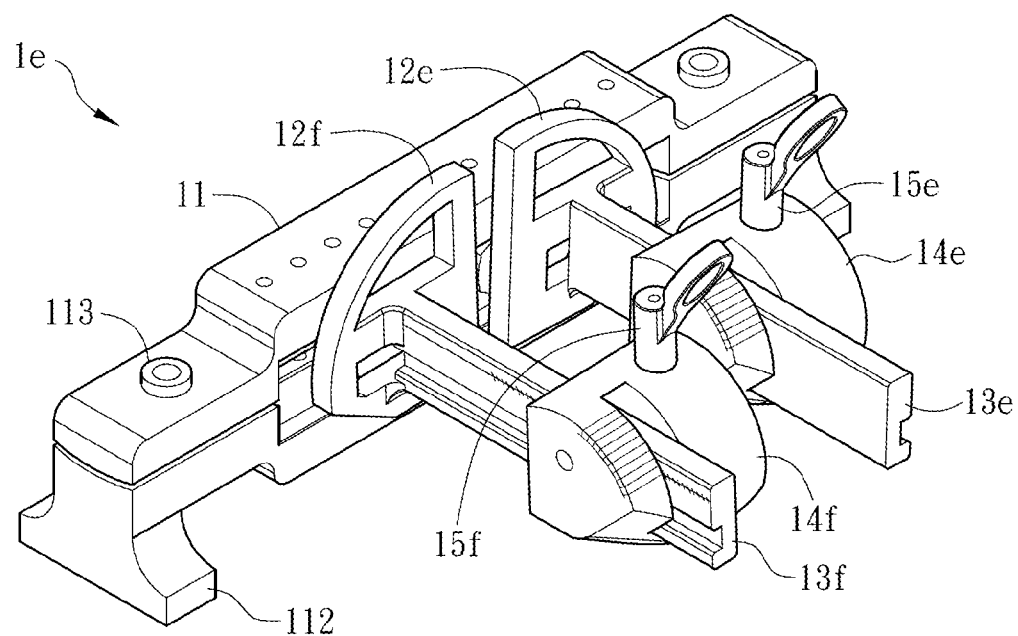
FIG. 6C is a schematic diagram showing another aspect of the assistant device for percutaneous puncture of FIG. 6B.

FIG. 6A is a schematic diagram showing an assistant device for percutaneous puncture according to a second embodiment of the invention, FIG. 6B is a schematic diagram showing an assistant device for percutaneous puncture according to a third embodiment of the invention, and FIG. 6C is a schematic diagram showing another aspect of the assistant device for percutaneous puncture of FIG. 6B. The assistant device 1a of FIG. 6A includes two second rotatable elements 14a and 14b, which are disposed at different sides of the fixing element 11a. The numbers of other related elements are adjusted corresponding to the two second rotatable elements 14a and 14b. For example, the fixing element 11a has two first rails 111a, and the assistant device 1a includes two first rotatable elements 12a and 12b and two supporting elements 13a and 13b. Accordingly, if two assistant restraint elements 15a and 15b are provided, it is possible to insert two pins 2 to perform the desired punctures at different positions. Preferably, the two pins 2 are aligned to two pedicles of a single vertebral body, and the assistant device 1a is helpful in the needed fixing, adjusting and correcting operations.

In an assistant device 1c of FIG. 6B, the two second rotatable elements 14c and 14d are disposed at the same side of the fixing element 11 for performing the desired punctures at two pedicles of two adjacent vertebral bodies. As shown in FIG. 6B, two assistant restraint elements 15c and 15d are configured adjacent to each other (the second rotatable elements 14c and 14d are configured opposite to each other). Of course, the two assistant restraint elements 15e and 15f may be disposed opposite to each other (the second rotatable elements 14e and 14f are configured at the same direction).

As mentioned above, the assistant device 1 of the invention may have different numbers and configurations of the first rotatable element(s), supporting element(s) and second rotatable element(s), which can be customized for benefiting the surgery. Of course, the number of the second rotatable elements 14 is not limited to the above embodiments. For example, three, four or more second rotatable elements 14 may be configured in the assistant device 1.

Figure 7:
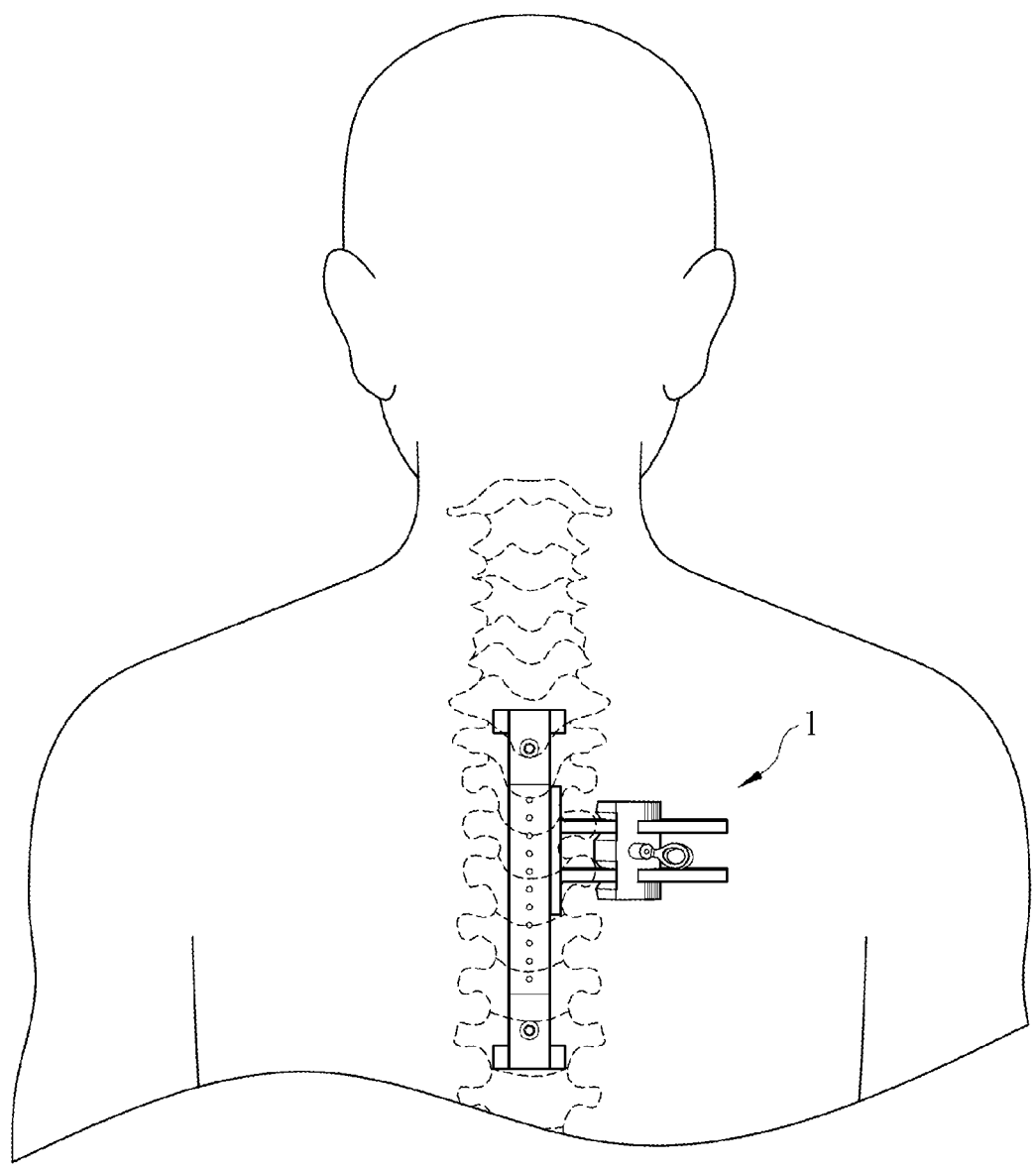
FIG. 7 is a schematic diagram showing the assistant device for percutaneous puncture fixed on the back of a patient.

FIG. 7 is a schematic diagram showing the assistant device for percutaneous puncture fixed on the back of a patient. Referring to FIG. 7, the fixing element 11 further includes a stand portion 112, which can fix the assistant device 1 on the patient's back around the target position by an attaching and non-invasive method. Then, the positions and angles of the first rotatable element 12 and the second rotatable element 14 are adjusted according to the operation plan. Finally, the assistant restraint element 15 is inserted into the puncture restraint pore 141, and then the pin 2 is inserted into the assistant restraint element 15 (see FIG. 5).

The puncture position and angle of the pin 2 can be captured by X-ray or C-arm for the following adjustment and correction. In practice, if the position of the pin 2 needs to be adjusted, the pin 2 is retrieved from the assistant restraint element 15 firstly, and then the first rotatable element 12 and/or the second rotatable element 14 are moved manually until the fixing element 11 and/or the supporting element 13 are adjusted to the desired position. Similarly, if the angle of the pin 2 needs to be adjusted, the first rotatable element 12 and/or the second rotatable element 14 are rotated manually. After the position and angle are all adjusted and corrected, the pin 2 is stuck into the patient's back and then passes through the pedicles to reach the inside of the vertebral body.

FIG. 8 is a schematic diagram showing a reaming member mounted on a pin. With reference to FIGS. 7 and 8 in view of the assistant device for percutaneous puncture of FIGS. 1 to 4B, after the puncture operation, the assistant restraint element 15 is removed and the reaming member 3 is mounted on the pin 2. The reaming member 3 includes a handheld portion 31 and a drill portion 32. To be noted, the shape and structure of the reaming member are not limited. For example, the reaming member can be a reaming or drilling device containing a handheld portion and a thread drill. In this embodiment, the reaming member is a T-shaped drilling member. Each of the pin 2 and the reaming member 3 can be a metal unit with better durability that is integrally formed or composed of separated parts. The reaming member 3 may further include a hollow portion 33 for accommodating the pin 2. The reaming member 3 is mounted on the pin 2 through the hollow portion 33, and then inserted into the pin restraint channel 152 and the puncture restraint pore 141.

As a result, the reaming member 3 is guided to the correct drilling position.

Figure 9:
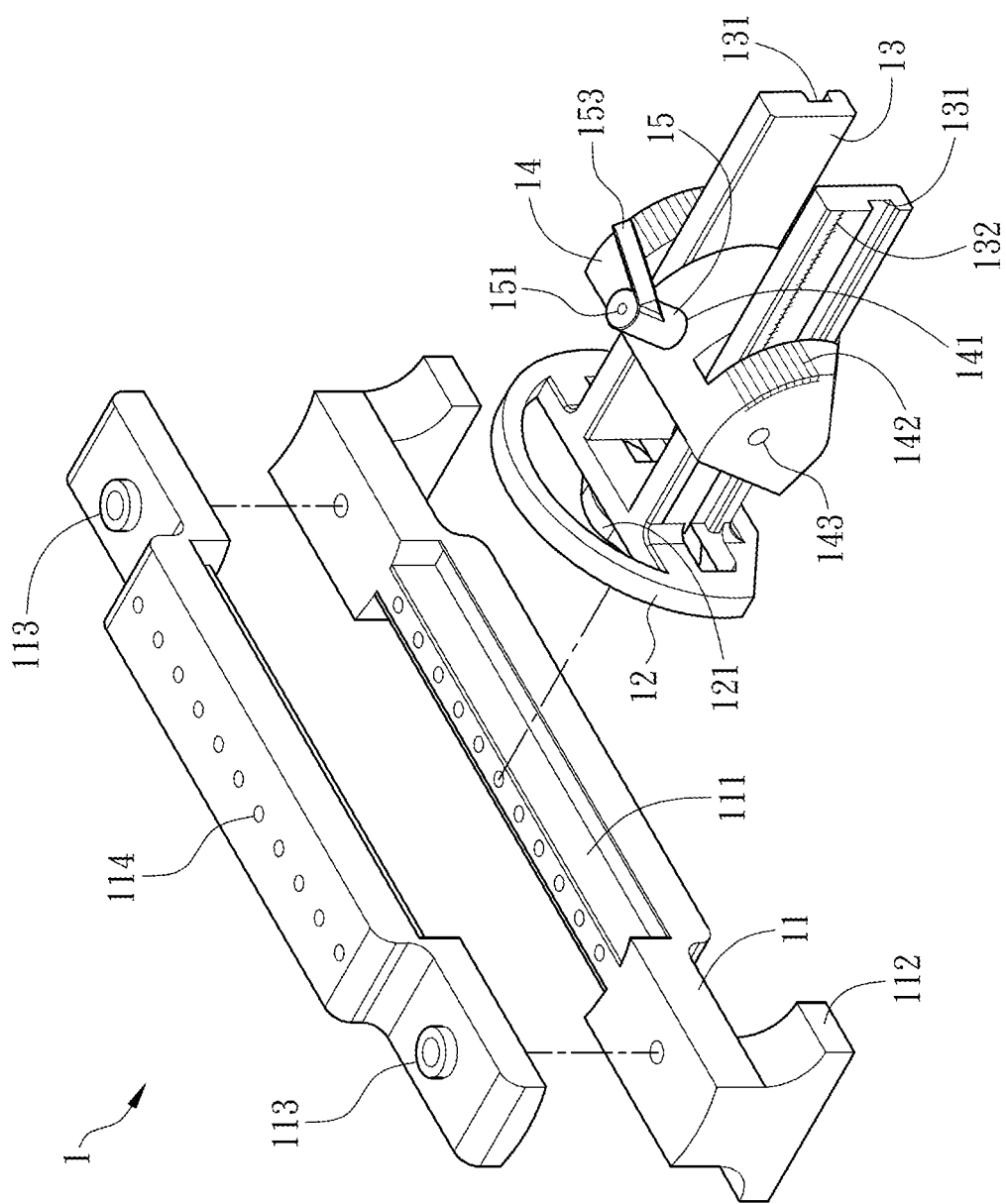
FIG. 9 is an exploded view of a fixing element of FIG. 1.

In addition, either the fixing element 11 has at least one fitting portion 113 or the second rotatable element 14 has at least one fitting portion 143. The fitting portion 113 of the fixing element 11 is configured for fixing the first rotatable element 12. In more specific, after the position and angle of the first rotatable element 12 are determined, the fitting portion 143 is manually operated to press two parts of the fixing element 11 to clip the first rotatable element 12. Thus, the first rotatable element 12 is locked and unmovable (see FIG. 9). The configuration of the fitting portion can provide sufficient stability for the following operation. Otherwise, the fitting portion 143 can be manually operated to fix the position and angle of the second rotatable element 14 relative to the supporting element 13, thereby further enhancing the desired stability.

In this embodiment, the fixing element 11 may further include a plurality of receiving holes 114 for receiving a plurality of pins 2. Similarly, the configurations of the receiving holes 114 can be also helpful to the following operation.

The present invention discloses an assistant device for percutaneous puncture, which has the same components and structure as the assistant device of the previously mentioned guiding assembly for percutaneous surgery, so the detailed descriptions thereof will be omitted here.

In summary, the assistant device for percutaneous puncture can be fixed on the back of a patient and cooperated with the pin and reaming member. By using the assistant device, the medical personnel does not need to hold the pin or reaming member all the time during the operation, thereby enhancing the stability and precision of the spinal surgery. More specific, the assistant device is helpful in guiding the pin to pedicles.

In the assistant device for percutaneous puncture, the first rotatable element is slidably disposed on the fixing element and the second rotatable element is slidably disposed on the supporting element, so that the first rotatable element is movable along a first axis and the second rotatable element is movable along a second axis. In practice, the operator can roughly place the assistant device around the target, and then fine adjust it for the precise operation. Moreover, the first rotatable element is rotatable about a first axis and the second rotatable element is rotatable about a second axis, so that the assistant device can adjust not only the puncture position but also the puncture angle, thereby precisely guiding the pin through the pedicle to reach the inside of vertebral body.

In addition, the supporting element is preferably configured with a distance mark portion, and the first or second rotatable element is preferably configured with an angle mark portion. Accordingly, the medical personnel can adjust or correct the puncture position and angle based on the numerical reference instead of doing these precise operations by the personal experience or intuition.

Moreover, the present invention is also helpful in reducing the radiation dose. In details, the assistant device for percutaneous puncture can provide a firmly and stably support, so that the medical personnel does not need to hold the pin all the time. Thus, the medical personnel can leave the photo room while taking X-ray or C-arm, thereby reducing the radiation dose took by the medical personnel. Regarding to the patient, since the adjusting and correcting times can be decreased, the total operation times of taking X-ray or C-arm are also decreased so as to reduce the radiation dose took by the patient. As a result, this invention can efficiently reduce the radiation dose took by the medical personnel and patient.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An assistant device for percutaneous puncture, comprising: a fixing element having a first rail; a first rotatable element slidably disposed on the first rail; a supporting element connected to the first rotatable element, wherein the supporting element extends along a first axis; and at least a second rotatable element slidably disposed on the supporting element and having a puncture restraint pore, wherein the fixing element extends along a second axis, the second rotatable element moves on the supporting element along the first axis, and second rotatable element is capable of rotating about an axis parallel to the second axis, and the second axis is perpendicular to the first axis, wherein the first rotatable element is rotatable about the first axis.

2. The assistant device according to claim 1, further comprising:
    an assistant restraint element having a pin restraint pore, wherein the assistant restraint element is disposed through the puncture restraint pore.

3. The assistant device according to claim 2, which is cooperated with a pin, wherein the pin is disposed through the pin restraint pore.

4. The assistant device according to claim 1, wherein the supporting element has a distance mark portion.

5. The assistant device according to claim 1, wherein the first rotatable element or the second rotatable element has an angle mark portion.

6. The assistant device according to claim 1, wherein the assistant device comprises two second rotatable elements disposed at different sides of the fixing element.

7. The assistant device according to claim 1, wherein the fixing element or the second rotatable element has at least a fitting portion.

8. The assistant device according to claim 1, wherein the fixing element further has a plurality of receiving holes for receiving a plurality of pins.

* * * * *